(12) United States Patent
Aceti et al.

(10) Patent No.: US 6,283,915 B1
(45) Date of Patent: Sep. 4, 2001

(54) DISPOSABLE IN-THE-EAR MONITORING INSTRUMENT AND METHOD OF MANUFACTURE

(75) Inventors: John Gregory Aceti, Cranbury; Marvin Allan Leedom, Princeton, both of NJ (US); Walter Paul Sjursen, Washington Crossing, PA (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/264,655

(22) Filed: Mar. 8, 1999

Related U.S. Application Data

(63) Continuation-in-part of application No. 08/815,852, filed on Mar. 12, 1997, now Pat. No. 5,881,159.

(51) Int. Cl.[7] ....................................................... A61B 5/00
(52) U.S. Cl. ......................... 600/300; 600/500; 600/559; 178/903
(58) Field of Search ....................................... 600/300–301, 600/481–486, 490, 500, 529–538; 128/900–905, 897–898; 340/573.1

(56) References Cited

U.S. PATENT DOCUMENTS

| | | |
|---|---|---|
| 3,527,901 | 9/1970 | Geib . |
| 3,598,928 | 8/1971 | Hickox . |
| 3,783,201 | 1/1974 | Weiss . |
| 4,539,440 | 9/1985 | Sciarra . |
| 4,639,556 | 1/1987 | Hartl et al. . |
| 4,712,245 | 12/1987 | Lyregaard . |
| 4,716,985 | 1/1988 | Haertl . |
| 4,870,688 | 9/1989 | Voroba et al. . |
| 4,969,534 | 11/1990 | Kolpe et al. . |
| 5,002,151 | 3/1991 | Oliveira et al. . |
| 5,012,520 | 4/1991 | Steegar . |
| 5,141,455 | 8/1992 | Ponn . |
| 5,146,051 | 9/1992 | Hermann . |
| 5,185,802 | 2/1993 | Stanton . |
| 5,213,099 | * 5/1993 | Tripp, Jr. .............................. 600/300 |
| 5,673,692 | * 10/1997 | Schulze et al. ...................... 600/300 |
| 6,004,274 | * 12/1999 | Nolan et al. ......................... 600/486 |
| 6,084,516 | * 7/2000 | Yasushi et al. .................... 340/573.1 |

\* cited by examiner

Primary Examiner—Eric F. Winakur
Assistant Examiner—Michael Astorino
(74) Attorney, Agent, or Firm—William J. Burke

(57) ABSTRACT

A disposable in-the-ear monitoring instrument includes a monitoring assembly for monitoring one or more vital health signs of a user, a transmitter assembly for transmitting the monitored vital health signs to a remote receiving unit, and a battery for energizing the assemblies. The assemblies and battery are mounted on a printed circuit which is disposed in a cylindrical shell. And the cylindrical shell is itself mounted in an earmold. The disposable in-the-ear monitoring instrument is of an optimum design having a minimum number of components, and thus is easy to assemble on an automated basis. The automated assembly of the in-the-ear monitoring instrument and its optimum design reduces costs and allows for the disposability of the monitoring instrument.

30 Claims, 4 Drawing Sheets

6,283,915 B1

DISPOSABLE IN-THE-EAR MONITORING INSTRUMENT AND METHOD OF MANUFACTURE

This Application is a continuation-in-part of application Ser. No. 08/815,852, filed Mar. 12, 1997, now U.S. Pat. No. 5,881,159.

FIELD OF THE INVENTION

The present invention is directed to an in-the-ear monitoring instrument and method of manufacture, and more particularly to an in-the-ear monitoring instrument that is small and inexpensive so as to be disposable, yet capable of monitoring one or more vital health signs of a user.

BACKGROUND OF THE INVENTION

Monitoring the vital health signs of a patient typically requires excessive time of medical personnel, or the patient being inconvenienced by being connected by wires to bulky monitoring equipment. For example, in a hospital setting, a nurse has to travel from patient-to-patient in order to determine such vital health signs as temperature and pulse. These account for a substantial amount of the nurse's time and do not provide continuous data. Continuously monitoring vital health signs may require the use of cumbersome and expensive equipment, and may cause the patient discomfort and inconvenience because this equipment has to be connected to the patient thereby limiting the patient's mobility. Both the time expended by medical personnel in obtaining vital health signs of patients, as well as the bulky equipment required, can account for a substantial cost in caring for patients.

It would therefore be desirable to have a simple low cost monitoring instrument which continuously or continually monitors a patients vital health signs and transmits these vital health signs to a remote monitoring unit without the need for the patient being physically connected to the monitoring unit. It would also be most desirous if the monitoring instrument was relatively non-intrusive to the patient and if the monitoring instrument were relatively inexpensive with regard to both the structure of its components and its method of manufacture. In addition, it would be desirable for such a monitoring instrument to have an integral power source and to be so inexpensive that it could be disposed of after its power source expires.

SUMMARY OF THE INVENTION

The present invention is directed to a disposable in-the-ear monitoring instrument including one or more transducers for sensing signals representing vital health signs of a user, electronics for processing the sensed signals, a transmitter for receiving the processed signals and transmitting the processed signals to a remote receiving unit where they can be processed to recover the vital health sign information, and a battery permanently electrically connected to the monitor electronics and transmitter and sealed in the monitoring instrument.

Another aspect of the present invention is a method for assembling the disposable in-the-ear monitoring instrument in which electrical components, various transducer components and batteries are connected to an elongated printed circuit strip thereby providing, on the strip, a plurality of assemblies. The strip is cut apart to form individual assembly types, each for a disposable in-the-ear monitoring instrument. Each assembly is placed in a cylindrical shell, and each shell is in-turn placed in an earmold of a soft, durable and compliant material.

BRIEF DESCRIPTION OF THE DRAWINGS

For a fuller understanding of the nature and objectives of the invention, reference should be made to the following detailed description, taken in connection with the accompanying drawings.

DETAILED DESCRIPTION

Figure 1:
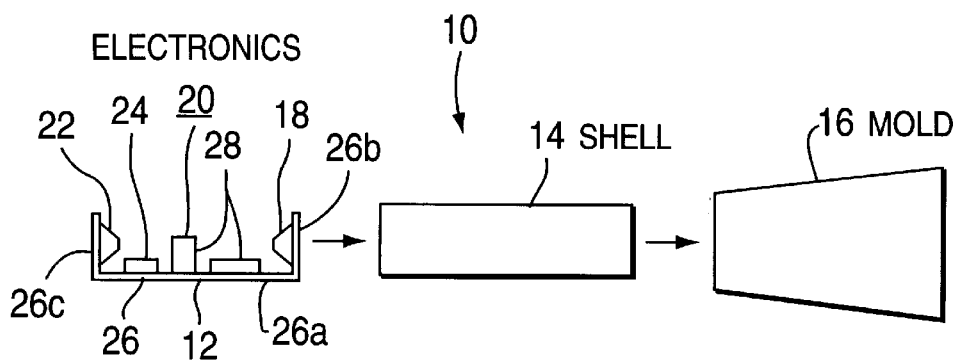
FIG. 1 is an exploded schematic view of the disposable hearing aid which is one embodiment of the present invention.
Figure 2:
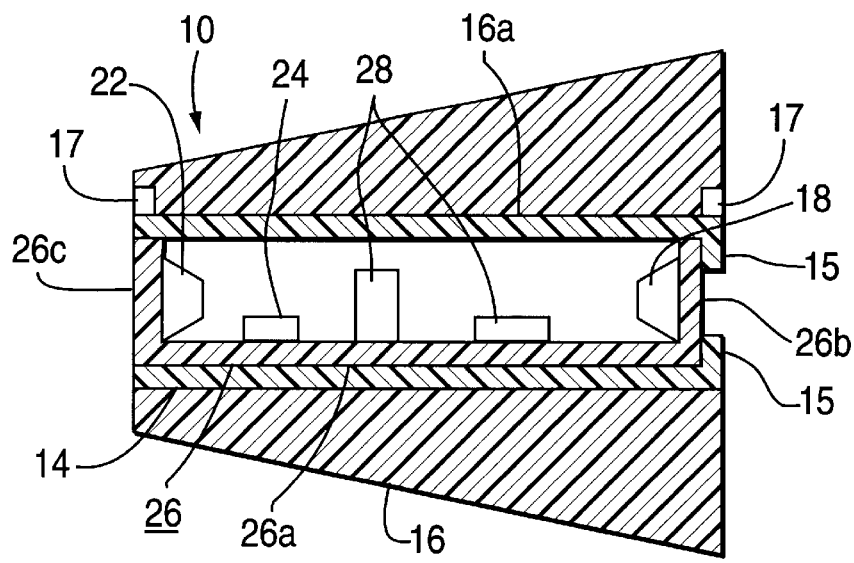
FIG. 2 is a cross-sectional view of the assembled disposable hearing aid.
Figure 3:
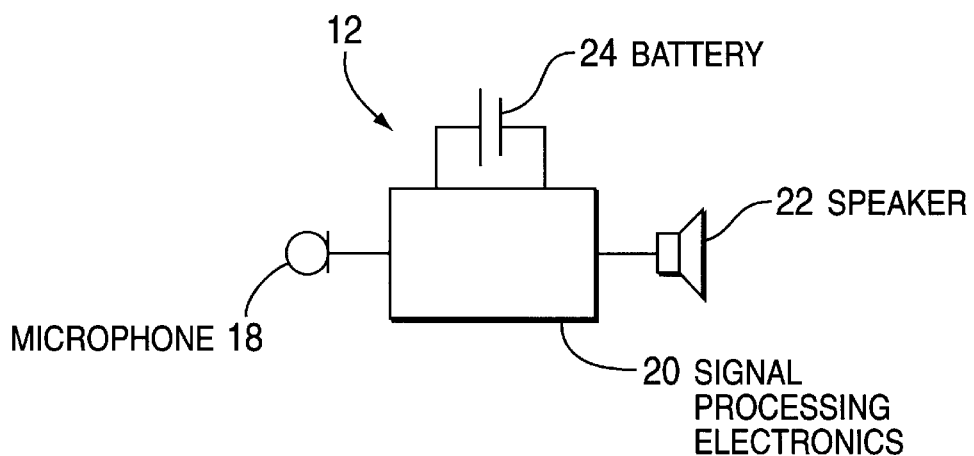
FIG. 3 is a schematic view of the electronics of the disposable hearing aid.

Referring initially to FIGS. 1 and 2 of the drawings, a hearing aid 10 is a first embodiment of the present invention. Hearing aid 10 comprises an electronic assembly 12, a shell 14 and an earmold 16. As shown in FIG. 3, the electronic assembly 12 includes a microphone 18 which is adapted to receive the sound and convert the sound into electrical signals. The microphone 18 is connected to the input of signal processing circuitry 20 which may, for example, amplify the sound, diminish any undesirable background noise and adjust the provided sound to compensate for particular deficiencies of a user. The output signals of the processing circuitry 20 is connected to a speaker, also known as a receiver, 22 which converts the output signals to sound and directs the sound into the ear of the user. A suitable battery 24 of any desired structure is mounted on the electronic assembly 12 and electrically connected to the signal processing circuitry 20 to operate the circuitry 20.

As shown in FIGS. 1 and 2, the electronics 12 include a printed circuit 26 having a base 26a and upright arms 26b and 26c at its ends. The printed circuit 26 also includes therein paths of a conductive metal (not shown). The microphone 18 is mounted on the upright arm 26b at one end of the printed circuit 26, and the receiver 22 is mounted on the upright arm 26c at the other end of the printed circuit 26. The components 28 of the signal processing circuitry 20 and the battery 24 are mounted on the base 26a of the printed circuit 26 between its ends. The microphone 18 can be any very small microphone which is presently on the market or can be a silicon microphone in which the diaphragm of the microphone 18 is a thin layer of silicon.

The signal processing circuitry 20 can be of any well known type which will provide the desired amplification.

For a very short operating hearing aid 10, such as for a three day operation, the signal processing circuitry 20 can be of the type which will provide amplification with fixed gain and frequency response. A simple, low-cost-class-A amplifier can be used. For a longer lasting hearing aid 10, such as a 30 day device, the signal processing circuitry 20 can be of the type which contains a two-channel amplifier with signal compression. One channel can process the lower frequency spectrum while the other channel can process the higher frequency spectrum. To extend battery life, a more efficient class-D amplifier can be used. For any type of signal processing circuitry 20, integrated circuits that perform the required signal processing should be used and are readily available. To achieve the different responses, different values of passive components, such as resistors and capacitors, can be used. The receiver 22 can be of any type of small speaker readily available. The battery 24 can be of any small type having sufficient power to operate the signal processing circuitry used.

The exemplary shell 14 is a flexible hollow cylindrical element that is adapted to house and protect the electronics 12. The shell 14 is of a molded, flexible plastic material and contains means, such as ribs 15 shown in FIG. 2, to orient and retain the electronics 12 therein. The shell 14 is of a material which protects the electronics 12 from moisture and mechanical damage. The shell 14 also provides acoustical features for facilitating incoming and outgoing sound, and has external features, such as ribs 17, which help retain it in the earmold 16.

Earmold 16 is of a soft, durable and compliant material. It can be of a cold-cured methacrylate, heat-cured methacrylate, heat-cured silicone, polyvinyl chloride copolymer or polyethylene co-polymer. The earmold 16 has an inner opening 16a into which the shell 14 containing the electronics 12 is inserted and retained. The outer configuration of the earmold 16, such as its shape and size, is such that it can be readily inserted in the ear canal of the user and which flexibly molds itself to the shape of the ear canal. Since the earmold 16 is of a compliant material, the pressure of the earmold 16 against the wall of the ear canal produces a good fit needed to prevent feedback and to help retain the hearing aid 10 in the ear. It has been found that earmolds of soft material are superior to those of hard material in the attenuation of feed back acoustics.

Figure 4:
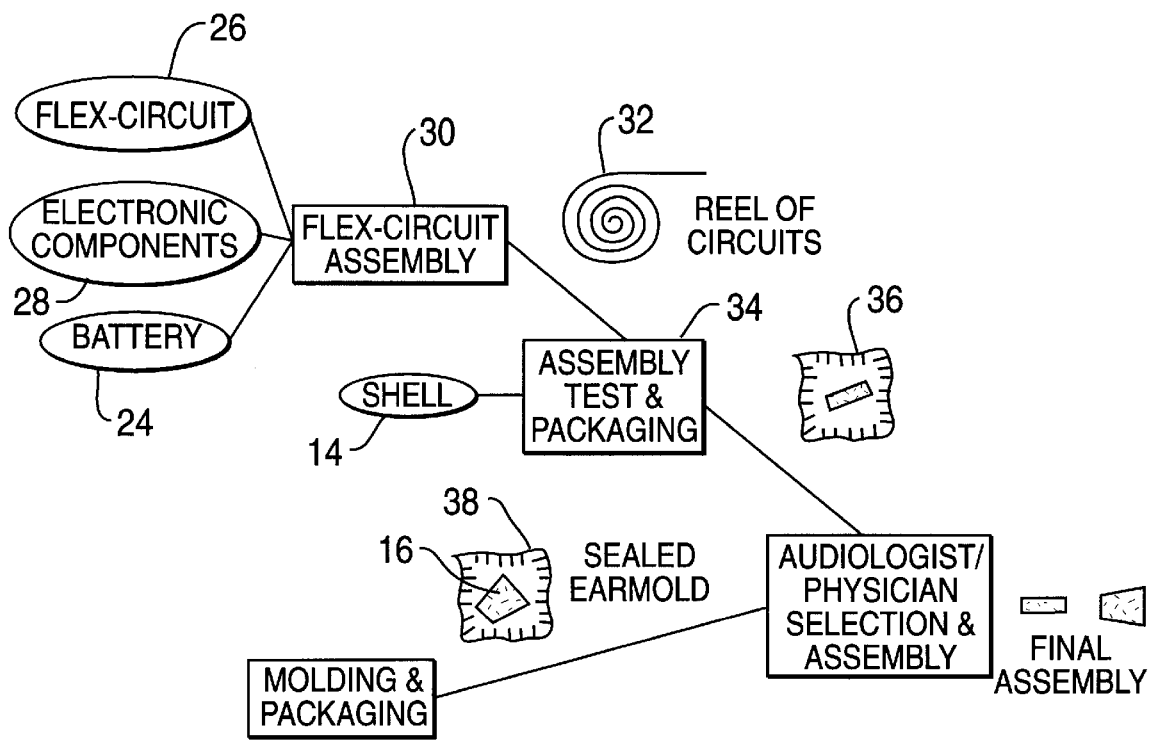
FIG. 4 is a flow chart showing a method of assembling the disposable hearing aid.

Referring to FIG. 4, there is illustrated a method of assembling the hearing aid 10 of the present invention. A flexible printed circuit 26 is feed from a reel along with the various components 28 which made up the electronics 12. Including microphones 18, receivers 22 and batteries 24, into an assembly apparatus 30. The assembly apparatus 30 assembles the components onto the flexible circuit to form a strip containing a plurality of the electronics 12. The completed assembly is mounted on a reel to form a reel 32 of the circuits.

The flexible circuit assemblies of the reel 32 are then fed along with shells 14 into an assembler 34 where the electronics 12 are cut apart from the reel, and each electronics 12 is formed and inserted into a shell 14. The shell assembly is then inserted into a package 36 which is hermetically sealed and contains a gas which will protect the shell assembly from the atmosphere and extinguish battery activity.

The earmolds 16 are molded in a suitable molding apparatus and packaged in a hermetically sealed package 38. The earmolds 16 are preferably molded in several different sizes so that a suitable size can be used for each user of the hearing aid 10.

Figure 5A:
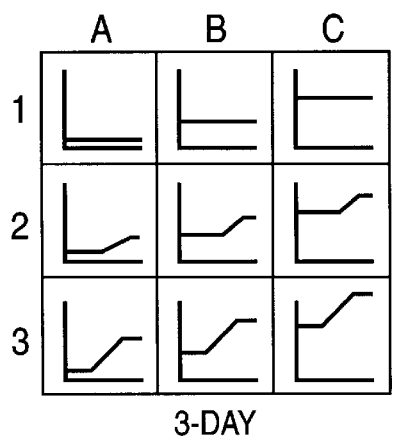
FIGS. 5a and 5b are charts showing the various responses of an amplifier circuit which can be used in the disposable hearing aid.
Figure 5B:
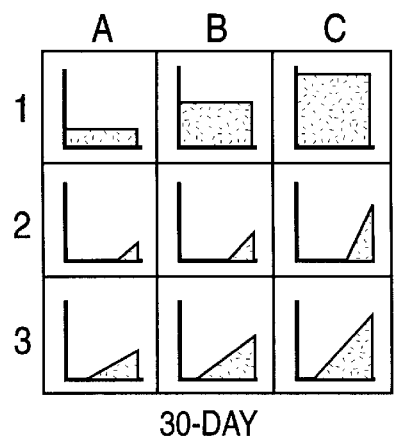

The signal processing circuitry 20 of the electronics 12 is designed to accommodate high-frequency hearing losses and flat-frequency hearing losses in the mild to moderate ranges. The signal processing circuitry 20 for different electronics 12 is made to provide different audiological responses. FIGS. 5a and 5b are charts showing the various responses which may be provided by the different electronics 12 that are made in the process of the present invention. FIG. 5a shows the responses for a three day device which has a fixed gain and frequency response, and FIG. 5b shows the responses for a 30 day device which has a two-channel amplifier. In each of FIGS. 5a and 5b, the columns represent different amplifier gains with column A being the lowest gain and column C being the highest gain. The rows represent different frequency responses with row 1 being a flat response, row 2 a mild high frequency boost and row 3 the moderate high frequency boost. Thus, in making the signal processing circuitry 20, different components are used so as to make up a fixed number of circuits having different gains and frequency responses as shown in FIGS. 5a and 5b. The different circuits are marked according to the charts of FIGS. 5a and 5b according to gain frequency response, such as A1, A2, A3, B1, etc.

The last step in making the hearing aid 10 of the present invention is done by an audiologist or physician after hearing of the user is tested and it is determined what type of audiological response is required. The audiologist or physician checks the charts shown in FIGS. 5a and 5b and picks the signal processing circuitry 20 which will provide the audiological response required by the user. The audiologist/physician then picks the shell assembly which contains the desired electronics, and picks an earmold 16 of the appropriate size for the user. The shell assembly is then inserted into the earmold 16 and the hearing aid 10 is ready to be inserted in the ear of the user.

In the hearing aid 10 of the present invention, the signal processing circuitry 20 has fixed audio characteristics and is made in a limited number of acoustical formats. Also, the acoustical format is preprogrammed in the electronics manufacture so that no potentiometers are needed for adjusting the circuit. In addition, the units are used only for the life of the battery. Thus, no on/off switch is used. Therefore, it is of simple design having a minimum number of components and is easy to assemble on an automatic basis. The signal processing circuitry 20 and the entire electronics 12 is inexpensive because they can be easily made in large volumes and economy of scale. The electronics 12 are encased in a simple hollow shell which is easy to assemble. Also, the earmold 16 is of simple design and of a soft, pliable material so as to be inexpensive. Thus, the entire hearing aid 10 is of a minimum number of inexpensive parts and is easy to assemble so that the hearing aid 10 is relatively inexpensive compared with presently used hearing aids. Since the hearing aid 10 is so inexpensive it is disposable. Therefore, when the battery 24 of the hearing aid 10 dies out, instead of replacing the battery 24, the whole hearing aid can be disposed of and replaced with a completely new hearing aid 10. Thus, there is provided by the present invention, a hearing aid 10 which is inexpensive to manufacture so as to be disposable. However, the hearing aid 10 still has all of the audio characteristics required by the user and has a high reliability. Furthermore, since the hearing aid of the present invention is small and has a soft, pliable earmold, it is more comfortable to wear. In addition, since it is disposable, it requires no service calls for cleaning or adjustment.

Figure 6:
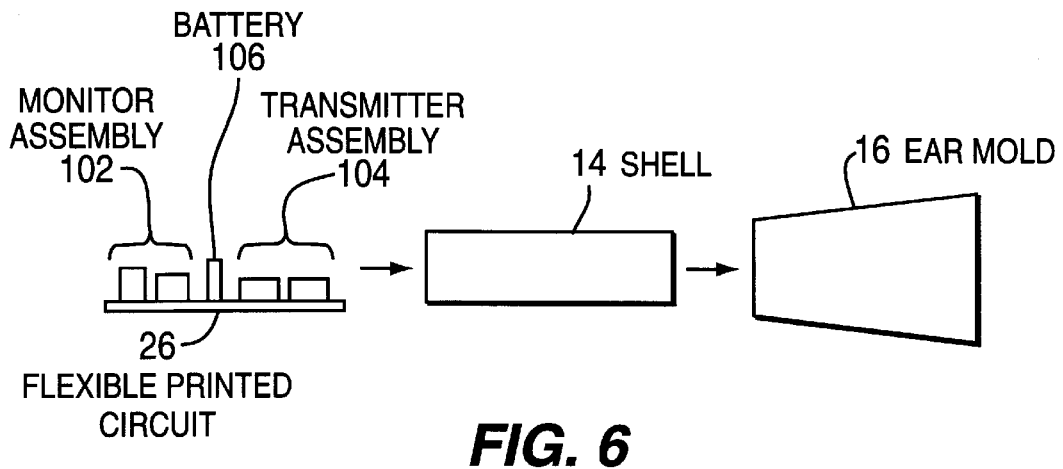
FIG. 6 is an exploded schematic view of a disposable in-the-ear monitoring instrument which is another embodiment of the present invention.
Figure 7:
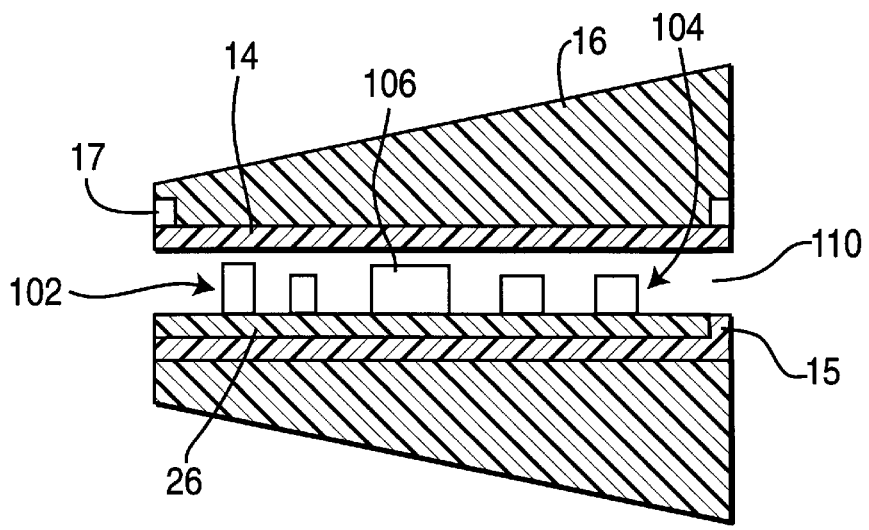
FIG. 7 is a cross-sectional view of the assembled disposable in-the-ear monitoring instrument.
Figure 8:
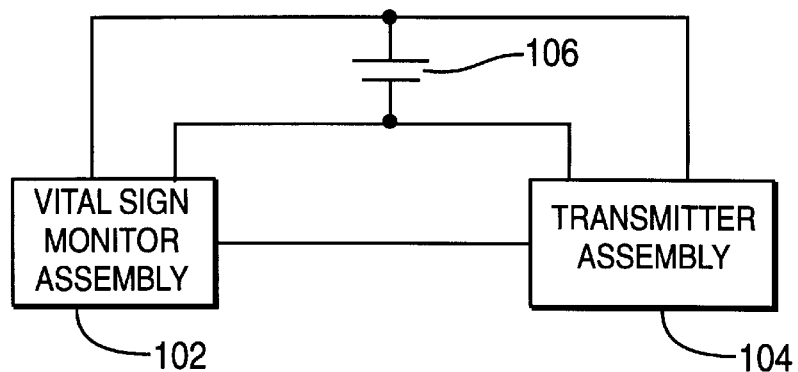
FIG. 8 is a schematic view of the monitor assembly, transmitter assembly and battery of the disposable in-the-ear monitoring instrument.
Figure 9:
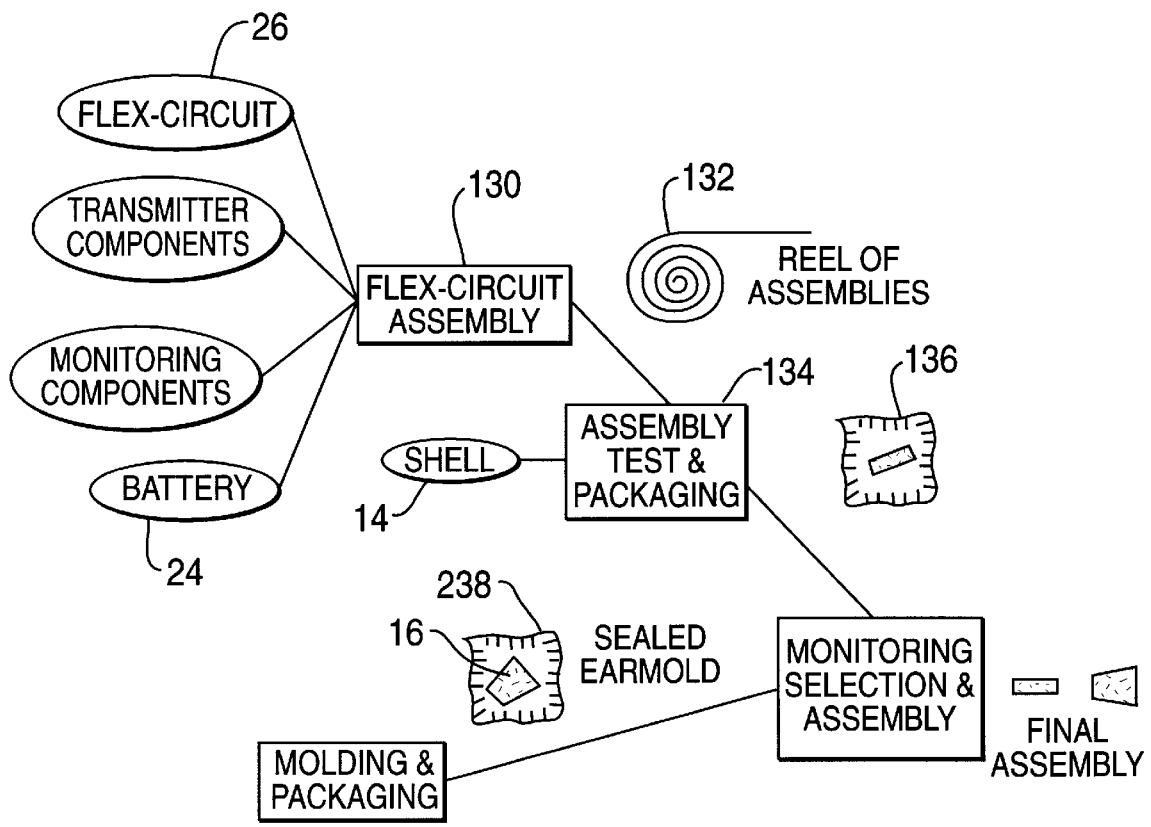
FIG. 9 is a flow chart showing a method of assembling the disposable in-the-ear monitoring instrument.

Shown in FIGS. 6–8 is a disposable in-the-ear monitoring instrument 100, which is a second embodiment of the present invention. FIG. 9 shows the assembly of monitoring instrument 100. FIG. 6 shows, as separated, the component elements of the disposable in-the-ear monitoring instrument 100, and FIG. 7 shows, as assembled, the disposable in-the-ear monitoring instrument 100. With respect to FIGS. 6–9, like numerals indicate like elements relative to the disposable hearing aid 10 of FIGS. 1–5.

The disposable in-the-ear monitoring instrument 100 includes a monitoring assembly 102, a transmitter assembly 104, and a battery disposed on a flexible printed circuit 26. Like the disposable hearing aid 10, the printed circuits 26 with the permanently mounted monitoring assembly 102, transmitter assembly 104, and battery is positioned within shell 14. And shell 14 is in-turn positioned within earmold 16.

The monitoring assembly 102 includes miniaturized component elements for monitoring one or more vital health signs of the individual using the disposable in-the-ear monitoring instrument 100. The components of monitoring assembly 102 are conventional components used for measuring such vital health signs as pulse, temperature, heart rate, respiration or blood oxygenation, for example. Thus monitoring assembly 102 may comprise sufficient components to monitor one vital health sign of the user, or a plurality of vital health signs. Such components could, for example, include transducers such as a miniaturized microphone (not shown) to monitor heart rate and respiration by conveying pulse sounds and respiration sounds from the ear canal to an external monitor, to aid in the auscultation of a patient; a thermistor (not shown), thermocouple (not shown) or other heat sensitive transducer (not shown) to measure the temperature in the ear canal; and one or more light sources (not shown) and one or more photo-active devices (e.g. photocells, phototransistors) (not shown) to determine blood oxygenation by monitoring the color of light that is reflected from the blood vessels in the eardrum.

Although the description above only describes a single type of monitoring transducer in each instrument, it is contemplated that multiple components may be combined. For example, an instrument may include a thermistor and a microphone, a microphone and a photocell or all three types of devices. Furthermore, it is contemplated that one transducer may be used to measure multiple vital health signs. For example, a microphone may be used to measure both pulse and respiration rates and the light source and photocell may be used to measure both pulse rate and blood oxygenation. It is known that composite acoustical signals derived through a microphone, as described above, can be analyzed into their original and independent sources based, for example, on their relative timing, frequency spectra, or average energy levels.

Transmitting assembly 104 is electrically connected to monitoring assembly 102 and receives electrical signals representative of the one or more vital health signs being monitored. Transmitting assembly 104 transmits these signals to a receiving unit or station (not shown) which may further process the signals and from which medical personnel can observe, and if necessary record the monitored vital health signs of the user. It is contemplated that the transmitting assembly may include digitizing circuitry which converts the analog signals to digital form prior to transmission or it may transmit the analog signals directly.

The receiving unit may include, for example, band pass filters which separate portions of a signal received from a microphone in the monitoring instrument into a pulse rate signal and a respiration signal. At the same time, these filters may attenuate ambient noise and other sounds from the person being monitored. The receiving unit may also include processing circuitry which analyzes color signals returned by the photocell or photocells in the monitoring instrument to determine blood oxygenation.

Sound signals provided by the monitoring unit to the receiving unit may be analyzed into component sounds to monitor normal vital health signs, in which case, an alarm condition may occur when the normal vital health signs are interrupted. Alternatively, the sound signals may be analyzed for abnormal conditions, such as fibrillation, arterial gallop, ventricular gallop, labored or rapid respiration or other abnormal sounds emitting from the heart or lungs, in which case an alarm condition may occur only when one of the abnormal sounds is detected.

Transmitter assembly 104 may comprise the components of any conventional transmitter such as an infrared transmitter, a radio wave transmitter, a microwave transceiver, or any combination of the foregoing. One type of microwave transceiver that can be used in monitoring instrument 100 conveys data by modulating the impedance of a microwave antenna. An exemplary transceiver of this type is disclosed in U.S. Pat. No. 5,491,482, entitled ELECTRONIC SYSTEM AND METHOD FOR REMOTE IDENTIFICATION OF CODED ARTICLES AND THE LIKE, which is incorporated herein by reference for its teaching on microwave transceivers. In the instance where the transmitter assembly 104 is a microwave transceiver, the remote monitoring unit may include an interrogator/reader unit which is capable of interrogating the microwave transceiver and which thereby can identify one individual using a particular disposable in-the-ear monitoring instrument 100 from among a plurality of individuals each of whom is using a disposable monitoring instrument. Alternatively, the transmitting assembly 104 may comprise an infrared diode which is modulated to transmit data from the monitoring instrument to the receiving unit as an infrared beam. For this type of transmitting assembly to operate most effectively, it is desirable for the infrared diode to be positioned in the opening of the ear canal in the concha. The transmitting assembly 104 may, alternatively, include a tunnel diode radio-frequency transmitter. To conserve power in any of these transmitter assemblies 104, it is contemplated that timing circuitry in the instrument 100 may periodically activate and then deactivate the transmitter assembly.

A suitable battery 106 is also disposed on or connected to the flexible printed circuit 26 and is connected to and thereby operates transmitter assembly 104. If necessary, battery 106 can also be connected to monitoring assembly 102 to operate any components of the monitoring assembly 102. FIG. 6 schematically shows battery 106 electrically connected to transmitter 104 and monitoring assembly 102. The particular battery 106 that will be used will depend on the desired operating life and the preferred operating voltage of the disposable in-the-ear monitoring instrument 100. Typically, a battery-life of 5 days is desired for monitoring instrument 100. Nonetheless extended battery life can result by utilizing more efficient components comprising the transmitter assembly 104 and monitoring assembly 102.

As shown in FIG. 7, the printed circuit 26, with monitoring assembly 102, transmitter assembly 104, and battery 106 permanently mounted thereon, is housed within and protected by the shell 14 which is a flexible hollow cylindrical element. Typically, shell 14 includes means such as ribs 15 to orient and retain printed circuit 26 and the monitoring and transmitter assemblies mounted thereon. In addition, shell 14 includes means, such as ribs 17, which mate with earmold 16 so that shell 14 is retained permanently within earmold 16. The outer configuration of earmold 16 is ribbed and of an appropriate size and shape to comfortably fit within the ear canal of the user, and because it is ribbed and of a soft, durable and compliant material, it will flexibly mold itself to the shape of the user's ear canal. Typically, only one size earmold 16 will be required to fit most adults. Because the earmold 16 is of a compliant material, it provides a good fit within the user's ear canal which assists the monitoring assembly 102 in providing accurate readings of the monitored vital health signs.

Extending longitudinally through the disposable in-the-ear monitoring instrument 100 is a hole 110 approximately 2 millimeters in diameter. Hole 110 provides venting when monitoring instrument 100 is disposed in the user's ear and also provides a means by which outside sounds enter the ear canal. Thus monitoring instrument 100 should not significantly affect the wearers hearing ability. In addition, it is anticipated that hearing aid 10, as shown in FIGS. 1–3, or a conventional hearing aid can also be incorporated in the disposable in-the-ear monitoring instrument 100. In such a configuration, hearing aid 10 may include a unity gain amplifier or may include an amplifier which compensates for a known hearing loss of the person being monitored.

Referring to FIG. 9, a method is shown of assembling the disposable in-the-ear monitoring instrument of the present invention. A flexible printed circuit 26 is fed from a reel to a flexible circuit assembly apparatus 130. Also fed to the flexible circuit assembly apparatus 130 are transmitter components comprising transmitter assemblies 104, and monitoring components comprising monitoring assemblies 102, as well as batteries 106. At the flexible circuit assembly apparatus, the components and batteries are assembled onto the printed circuit 26 to form a strip containing a plurality of individual assemblies intended for the manufacture of a plurality of disposable in-the-ear monitoring instruments 100. The completed assemblies are mounted on a reel of assemblies 132.

The assemblies comprising reel 132 are then fed along with shells 14 into an assembler 134 where each individual assembly is cut apart from the reel 132, and is installed in a shell 14. The shell assembly is then inserted into a package 136 which is hermetically sealed and contains a gas which protects the shell assembly from the atmosphere, and also suspends battery activity. Thus, at this point in the assembly of the disposable in-the-ear monitoring instrument, each shell 14 contains components capable of monitoring one or a plurality of pre-selected vital health signs and a miniaturized transmitter capable of transmitting signals representing the monitored vital health signs to a remote monitoring unit.

In a separate manufacturing step, earmolds 16 are molded and packaged in a hermetically sealed package 138. Earmolds 16 are typically molded in one size suitable to accommodate most adult users. Alternatively, because earmolds 16 are compliant, a relatively small number of different sized earmolds may be made to accommodate substantially all prospective users.

In the last step of the assembly process, a physician or other medical personnel determines the vital health signs which are to be monitored and thereby selects a shell containing a monitoring assembly capable of determining such vital health signs, and places that shell 14 into an earmold 16. Thus for example if only the user's pulse is to be monitored, a shell containing a pulse monitoring assembly would be selected, but if, for example, both the user's pulse and blood oxidation is to be monitored, another shell 14 containing an appropriate monitoring assembly would be selected.

The disposable in-the-ear monitoring instrument 100 is used only for the life of the battery permanently housed therein. Accordingly, there is no need for an on/off switch, especially if a metal-air type battery, such as a zinc-air battery, is used. Removing the monitor from the sealed package would activate the battery and the devices would continue to operate until the battery is depleted. The overall design of the monitoring assembly 102 and transmitter assembly 104 are purposely kept relatively simple using a minimum number of components to accommodate automated assembly. Thus, the monitoring assembly 102 and transmitter assembly 104 are inexpensive because they can be manufactured in large volumes resulting in an economy of scale. In addition, the monitoring assembly 102 and transmitter assembly 104 are easily encased in the simple hollow shell 14. Furthermore, earmold 16 is of a simple design and of a soft, pliable material so that it too is inexpensive.

The resulting disposable in-the-ear monitoring instrument 100 is of a minimum number of inexpensive parts, easily assembled, easy to use and relatively inexpensive compared with presently used monitoring instruments, which are much more complex and cumbersome to use. A clear advantage, therefore, of the present invention is its disposability. That is, once the battery in the monitoring instrument 100 has expired, the unit is disposed and replaced with a new monitoring instrument 100. The disposability of the monitoring instrument also aids in preventing the spread of disease.

Although the disposable in-the-ear monitoring instrument 100 is inexpensive and simpler to use than conventional monitoring instruments, it is nonetheless highly reliable. In addition to its disposability and relatively low cost, the monitoring instrument 100 of the present invention is also more comfortable for the user than other presently used monitoring instruments.

Although the present invention has been described in relation to particular embodiments thereof, many other variations and modifications will become apparent to those skilled in the art. It is preferred, therefore, the present invention be limited not by the specific disclosure herein, but only by the appended claims.

What is claimed:

1. A disposable in-the-ear monitoring instrument, comprising:
    one or more transducers for monitoring vital health signs of a user,
    a transmitter for receiving signals from said one or more transducers representative of monitored vital health signs and for transmitting said signals to a remote location,
    a battery permanently electrically connected to the transmitter; and
    an earmold of a soft pliable material surrounding the one or more transducers and the transmitter and adapted to fit into and mold to the ear of a user.

2. The disposable in-the-ear monitoring instrument of claim 1, wherein said one or more transducers include a microphone for translating audio signals caused by blood flowing through the user's blood vessels into electrical signals.

3. The disposable in-the-ear monitoring instrument of claim 1, wherein said one or more transducers include at least one light source and at least one photodetector which senses color of blood vessels in the user's ear drum and translates the sensed color into electrical signals.

4. The disposable in-the-ear monitoring instrument of claim 1, wherein said one or more transducers include a heat sensitive transducer which senses temperature and translates the sensed temperature into an electrical signal.

5. The disposable in-the-ear monitoring instrument of claim 1, wherein said one or more transducers include a microphone for auscultating the user's pulse.

6. The disposable in-the-ear monitoring instrument of claim 1, wherein said one or more transducers include a microphone for auscultating the user's respiration.

7. The disposable in-the-ear monitoring instrument according to claim 1, wherein said one or more transducers include a microphone for auscultating the user's lung sounds to detect abnormal respiratory sounds.

8. The disposable in-the-ear monitoring instrument according to claim 1, wherein said one or more transducers include a microphone for auscultating the user's heart to detect fibrillation, arterial gallop, ventricular gallop or other abnormal sounds emitting from the heart.

9. The disposable in-the-ear monitoring instrument of claim 1, wherein said transmitter is a radio frequency transmitter.

10. The disposable in-the-ear monitoring instrument of claim 1, wherein said transmitter is an infrared transmitter.

11. The disposable in-the-ear monitoring instrument of claim 1, wherein said transmitter is a microwave transceiver.

12. The disposable in-the-ear monitoring instrument of claim 1, further comprising a shell surrounding said one or more transducers and said transmitter and adapted to fit within said earmold.

13. The disposable in-the-ear monitoring instrument of claim 12, wherein the shell is a flexible, hollow cylindrical element.

14. The disposable in-the-ear monitoring instrument of claim 12, wherein the shell includes means to orient and retain the one or more transducers and the transmitter.

15. The disposable in-the-ear monitoring instrument of claim 13, wherein the earmold is of a soft pliable material selected from the group of cold-cured methacrylate, heat-cured methacrylate, heat-cured silicone, polyvinyl chloride copolymer and polyethylene co-polymer.

16. The disposable in-the-ear monitoring instrument of claim 1 further comprising a printed circuit board on which said one or more transducers and said transmitter are mounted and electrically connected together.

17. The disposable in-the-ear monitoring instrument of claim 1, wherein said battery is electrically connected to said one or more transducers.

18. The disposable in-the-ear monitoring instrument of claim 1, having an opening therethrough for transmission of sound to the user.

19. The disposable in-the-ear monitoring instrument of claim 1, further comprising a hearing aid.

20. The disposable in-the-ear monitoring instrument of claim 19, wherein said hearing aid includes a unity gain amplifier.

21. A disposable in-the-ear monitoring instrument, comprising:
    an electronic printed circuit board;
    a battery, permanently mounted to the electronic printed circuit board;
    one or more monitors for monitoring vital health signs of a user, said one or more monitors permanently mounted to the electronic printed circuit board;
    a transmitter for receiving from said one or more monitors a signal representative of a monitored vital health sign of said user and transmitting said signal to a remote location, said transmitter being coupled to the battery;
    a shell into which the electronic printed circuit board, with said battery, said one or more transducers and said transmitter, is inserted; and
    an earmold of a soft pliable material surrounding the shell and adapted to fit into and mold the ear of said user.

22. The disposable in-the-ear monitoring instrument of claim 21, wherein said one or more transducers are coupled to said battery.

23. A method of making a disposable in-the-ear monitoring instrument, comprising the steps of:
    mounting electrical components, monitoring components and batteries onto an elongated printed circuit strip to form there along respective assemblies of a plurality of disposable in-the-ear monitoring instruments;
    cutting the printed circuit strip apart to form individual assemblies of one or more monitors, transmitter and battery of a disposable in-the-ear monitoring instrument on a printed circuit;
    inserting each assembly into a separate cylindrical shell; and
    inserting a shell containing an assembly into an opening in an earmold of a soft, durable and complaint material.

24. The method of claim 23, wherein after said electrical components, monitoring components and batteries are mounted on said flexible printed circuit strip, said strip is mounted on a reel.

25. The method of claim 24, wherein said flexible printed circuit strip on said reel is fed with shells into an assembler which cuts the strip apart into said individual assemblies and inserts each assembly into a separate shell.

26. The method of claim 25, wherein after said assemblies are inserted into said shells, said shells containing said assemblies are disposed into respective packages which are hermetically sealed and which contain a gas, whereby the casings and assemblies are protected from atmospheric contamination and any electrical activity in the batteries is significantly reduced.

27. The method of claim 26, wherein said earmolds are molded and packaged in an hermetically sealed package.

28. The method of claim 27, wherein a suitable earmold and shell suitable for monitoring one or more vital health signs are removed from their individual packages and assembled to form a disposable in-the-ear monitoring instrument.

29. The method of claim 23, wherein said monitoring components are assembled onto said elongated printed circuit strip to form individual monitoring assemblies capable of monitoring, for a particular user, one or a plurality of vital health signs of the user.

30. The method of claim 29, wherein said earmolds are made in a predetermined number of different sizes, and a shell suitable for the particular monitoring needs of the user is inserted into an earmold of an appropriate size for the user.

* * * * *